US010898461B2

(12) United States Patent
Gaillard et al.

(10) Patent No.: US 10,898,461 B2
(45) Date of Patent: Jan. 26, 2021

(54) SALTS OF 3-[(DIMETHYLAMINO)METHYL]-N-{2-[4-(HYDROXYCARBAMOYL)PHENOXY]ETHYL}-1-BENZOFURAN-2-CARBOXAMIDE, RELATED CRYSTALLINE FORMS, METHOD FOR PREPARING THE SAME AND PHARMACEUTICAL COMPOSITIONS CONTAINING THE SAME

(71) Applicant: Pharmacyclics LLC, Sunnyvale, CA (US)

(72) Inventors: Marina Gaillard, Orleans (FR); Philippe Letellier, Orleans (FR)

(73) Assignee: Pharmacyclics LLC, Sunnyvale, CA (US)

( * ) Notice: Subject to any disclaimer, the term of this patent is extended or adjusted under 35 U.S.C. 154(b) by 0 days.

(21) Appl. No.: 16/676,911

(22) Filed: Nov. 7, 2019

(65) Prior Publication Data
US 2020/0069637 A1 Mar. 5, 2020

Related U.S. Application Data

(63) Continuation of application No. 15/508,609, filed as application No. PCT/US2015/048243 on Sep. 3, 2015, now abandoned.

(30) Foreign Application Priority Data

Sep. 3, 2014 (FR) ...................................... 14 58215
Sep. 3, 2014 (FR) ...................................... 14 58224

(51) Int. Cl.
| | |
|---|---|
| *A61K 31/343* | (2006.01) |
| *C07D 307/85* | (2006.01) |
| *A61K 31/135* | (2006.01) |
| *A61K 31/166* | (2006.01) |
| *A61K 31/185* | (2006.01) |
| *G01N 23/20* | (2018.01) |
| *G01V 3/14* | (2006.01) |

(52) U.S. Cl.
CPC .......... *A61K 31/343* (2013.01); *A61K 31/135* (2013.01); *A61K 31/166* (2013.01); *A61K 31/185* (2013.01); *C07D 307/85* (2013.01); *G01N 23/20* (2013.01); *G01V 3/14* (2013.01)

(58) Field of Classification Search
CPC .. A61K 31/343; A61K 31/135; A61K 31/166; A61K 31/185; G01N 23/20; G01V 3/14; C07D 307/85; A61P 35/02; A61P 35/00; A61P 25/00; A61P 21/00; A61P 17/00; C07B 2200/13
See application file for complete search history.

(56) References Cited

U.S. PATENT DOCUMENTS

| | | | |
|---|---|---|---|
| 3,038,004 | A | 6/1962 | Copp et al. |
| 6,489,343 | B2 | 12/2002 | Castro Pineiro et al. |
| 7,276,612 | B2 | 10/2007 | Verner et al. |
| 9,115,108 | B2 | 8/2015 | Pimont-Garro et al. |
| 10,150,748 | B2 | 12/2018 | Pimont-Garro et al. |
| 2005/0187261 | A1 | 8/2005 | Verner et al. |
| 2007/0005039 | A1 | 1/2007 | Biggs et al. |
| 2011/0311624 | A1 | 12/2011 | Loury et al. |
| 2013/0005980 | A1 | 1/2013 | Jaryal et al. |
| 2014/0057862 | A1 | 2/2014 | Lory et al. |
| 2014/0194479 | A1 | 7/2014 | Schmauss et al. |
| 2014/0249215 | A1 | 9/2014 | Pimont-Garro et al. |
| 2017/0313671 | A1 | 11/2017 | Pimont-Garro et al. |
| 2020/0069637 | A1 | 3/2020 | Gaillard et al. |

FOREIGN PATENT DOCUMENTS

| | | |
|---|---|---|
| AU | 2014224456 A1 | 10/2015 |
| EP | 2964622 A1 | 1/2016 |
| EP | 3252044 A1 | 12/2017 |
| WO | WO-2004/092115 A2 | 10/2004 |
| WO | WO-2005/063713 A1 | 7/2005 |
| WO | WO-2010/123507 A1 | 10/2010 |

(Continued)

OTHER PUBLICATIONS

Badawy et al., "Salt selection for pharmaceutical compounds," Drugs Pharm Sci, 178: 63-80 (2008).
Bastin et al., "Salt selection and optimisation procedures for pharmaceutical new chemical entities," Org Process Res Dev, 4(5): 427-435 (2000).
Berge et al., "Pharmaceutical Salts," J Pharm Sci, 66(1): 1-19 (1977).

(Continued)

*Primary Examiner* — Matthew P Coughlin
*Assistant Examiner* — Thurman Wheeler
(74) *Attorney, Agent, or Firm* — Foley Hoag LLP

(57) ABSTRACT

Described herein are salts of 3-[(dimethylamino)methyl]-N-{2-[4-(hydroxycarbamoyl)phenoxy]ethyl}-1-benzofuran-2-carboxamide, in particular that of formula (I):

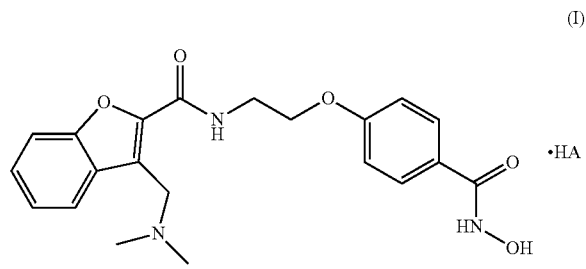

(I)

wherein HA is naphthalene-1,5-disulfonic acid, naphthalene-2-sulfonic acid, oxalic acid, benzenesulfonic acid, or sulfuric acid, or hydrates thereof, and crystalline forms thereof characterized by the powder X-ray diffraction diagram and the 13C CP/MAS NMR solid state spectrum. Also described are compositions, methods of use and preparation thereof.

4 Claims, No Drawings

(56) References Cited

FOREIGN PATENT DOCUMENTS

WO    WO-2013/004965 A1    1/2013
WO    WO-2014/135776 A1    9/2014

OTHER PUBLICATIONS

Buggy et al., "CRA-024781: a novel synthetic inhibitor of histone deacetylase enzymes with antitumor activity in vitro and in vivo," Mol Cancer Ther. 5(5):1309-1317 (2006).

Caira, "Crystalline Polymorphism of Organic Compounds," Topics in Current Chemistry, 198:163-208 (1998).

French Preliminary Search Report for FR1351898 dated Oct. 30, 2013.

Gould, "Salt selection for basic drugs," Int J Pharm, 33(1-3): 1-274 (1986).

H.G. Brittain, "Polymorphism in Pharmaceutical Solids", Second Edition, Informa Healthcare, NY, 2009.

International Preliminary Report on Patentability for PCT/FR2014/050455 dated Sep. 8, 2015.

International Search Report and Written Opinion for International Application No. PCT/US2015/048243 dated Nov. 11, 2015.

International Search Report and Written Opinion for PCT/FR2014/050455 dated May 8, 2014.

Morris et al., "An integrated approach to the selection of optimal salt form for a new drug candidate," Int J Pharm, 105(3): 209-217 (1994).

Neau, "Pharmaceutical Salts," Water-Insoluble Drug Formulation, 2: 417-435 (2008).

*Pfizer, Inc,* v. *Apotex*, 480 F.3d 1348, *; 2007 U.S. App. Lexis 6623, **; 82 U.S.P.Q.2D (BNA) 1321: p. 1-13.

Sawant et al., "Necessity of Establishing Chemical Integrity of Polymorphs of Drug Substance Using a Combination of NMR, HPLC, Elemental Analysis, and Solid-State Characterization Techniques: Case Studies," Org Process Res Dev, 17(3):519-532 (2013).

Serajuddin, "Salt formation to improve drug solubility," Adv Drug Deliv Rev, 59(7): 603-616 (2007).

Stahl et al., Handbook of Pharmaceutical Salts: Properties, Selection and Use, 2002.

Swarbrick et al., "Salt Forms of Drugs and Absorption," Encyclopedia of Pharmaceutical Technology, 13: 453-499 (1988).

SALTS OF 3-[(DIMETHYLAMINO)METHYL]-N-{2-[4-(HYDROXYCARBAMOYL) PHENOXY]ETHYL}-1-BENZOFURAN-2-CARBOXAMIDE, RELATED CRYSTALLINE FORMS, METHOD FOR PREPARING THE SAME AND PHARMACEUTICAL COMPOSITIONS CONTAINING THE SAME

CROSS-REFERENCE TO RELATED APPLICATIONS

This application is a continuation of U.S. patent application Ser. No. 15/508,609, filed Mar. 3, 2017, which is the U.S. National Stage of PCT/US2015/048243, filed Sep. 3, 2015, which claims the benefit of French Patent Application Nos. 1458215 and 1458224, both filed Sep. 3, 2014, the contents of each of which are incorporated herein by reference in their entirety.

FIELD OF THE INVENTION

The present invention relates to novel salts of 3-[(dimethylamino)methyl]-N-{2-[4-(hydroxycarbamoyl)phenoxy]ethyl}-1-benzofuran-2-carboxamide or hydrates or polymorphs thereof, methods for preparing the same as well as pharmaceutical compositions and uses thereof.

BACKGROUND OF THE INVENTION

3-[(Dimethylamino)methyl]-N-{2-[4-(hydroxycarbamoyl)phenoxy]ethyl}-1-benzofuran-2-carboxamide, also referred to as abexinostat, is a histone deacetylase (HDAC) inhibitor which is described in the patent application WO 2004/092115. It was shown to inhibit cell growth and induce apoptosis in tumor cells cultural in vitro, and inhibit tumor growth in vivo in xenograft models (Buggy et al., *Mol. Cancer Ther.* 2006, 5(5), 1309). Given its pharmacological profile, abexinostat is intended to be used in the treatment of cancer.

SUMMARY OF THE INVENTION

The present invention relates to novel salts of 3-[(dimethylamino)methyl]-N-{2-[4-(hydroxycarbamoyl)phenoxy]ethyl}-1-benzofuran-2-carboxamide or hydrates or crystalline forms thereof, methods for preparing or using the same as well as pharmaceutical compositions containing the same.

More particularly, the invention relates to salts of 3-[(dimethylamino)methyl]-N-{2-[4-(hydroxycarbamoyl)phenoxy]ethyl}-1-benzofuran-2-carboxamide of formula (I):

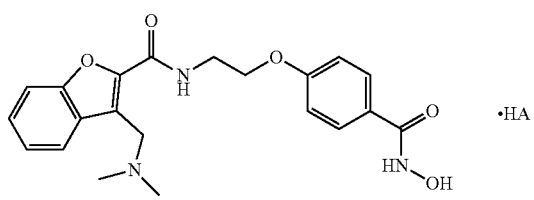

(I)

in which HA is naphthalene-1,5-disulfonic acid, naphthalene-2-sulfonic acid, oxalic acid, benzenesulfonic acid, or sulfuric acid or hydrates thereof.

The present invention also relates to novel crystalline forms of the salts of 3-[(dimethylamino)methyl]-N-{2-[4-(hydroxycarbamoyl)phenoxy]ethyl}-1-benzofuran-2-carboxamide of formula (I), methods for preparing the same as well as pharmaceutical compositions containing the same, and uses thereof.

These and other aspects and embodiments are described in following detailed description.

DETAILED DESCRIPTION OF THE INVENTION

It should be understood that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The patent application WO 2004/092115 describes two different access routes for producing 3-[(dimethylamino)methyl]-N-{2-[4-(hydroxycarbamoyl)phenoxy]ethyl}-1-benzofuran-2-carboxamide. In both cases, 3-methylbenzofuran-2-carboxylic acid is used as the starting material, but the functionalization of this central ring by the dimethylamino group in position 3 is carried out at different stages of the synthesis processes, before or after the coupling of the derivative of benzofuran-2-carboxylic acid with methyl 4-(2-aminoethoxy)benzoate. The application WO 2004/092115 specifically describes the production of the hydrochloride of 3-[(dimethylamino)methyl]-N-{2-[4-(hydroxycarbamoyl)phenoxy]ethyl}-1-benzofuran-2-carboxamide. However, the use of this salt on an industrial scale is difficult because of its hygroscopic properties.

From an industrial point of view, it is important to be able to synthesize the compound with excellent purity, anti in particular in a highly reproducible form, exhibiting valuable properties of dissolution, nitration, drying, ease of formulation and stability enabling the prolonged storage thereof without specific temperature, light, humidity or oxygen level conditions.

In one aspect, the present invention relates to naphthalene-1,5-disulfonic acid, naphthalene-2-sulfonic acid, oxalic acid, benzenesulfonic acid, or sulfuric acid salts of 3-[(dimethylamino)methyl]-N-{2-[4-(hydroxycarbamoyl)phenoxy]ethyl}-1-benzofuran-2-carboxamide or one of the hydrates thereof, a method for preparing the same as well as pharmaceutical compositions containing the same, and uses thereof.

In one aspect, the invention relates to salts of 3-[(dimethylamino)methyl]-N-{2-[4-(hydroxycarbamoyl)phenoxy]ethyl}-1-benzofuran-2-carboxamide of formula (Ia):

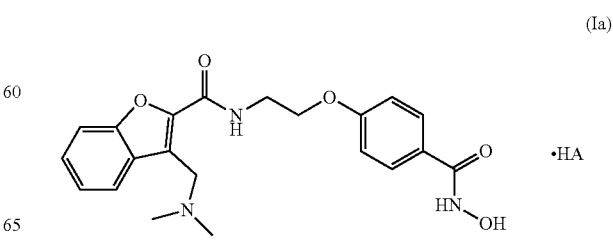

(Ia)

in which HA is naphthalene-1,5-disulfonic acid, naphthalene-2-sulfonic acid, oxalic acid or benzenesulfonic acid.

In another aspect, the subject matter of the invention relates to the hydrogen sulfate of 3-[(dimethylamino)methyl]-N-{2[4-(hydroxycarbamoyl)phenoxy]ethyl}-1-benzofuran-2-carboxamide of formula (Ib):

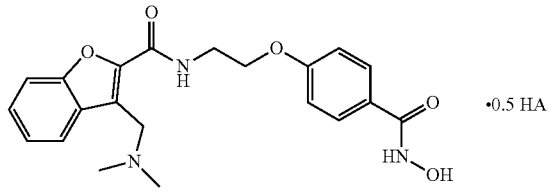

(Ib)

wherein HA is sulfuric acid, as well as hydrates thereof.

The present invention also describes methods for producing salts of 3-[(dimethylamino)methyl]-N-{2-[4-(hydroxycarbamoyl)phenoxy]ethyl}-1-benzofuran-2-carboxamide in well-defined and reproducible crystalline forms or hydrated crystalline forms, exhibiting very good stability compatible with the industrial constraints on preparation (in particular, drying) and storage of pharmaceutical compositions.

In one aspect, provided is a crystalline form of the naphthalene-1,5-disulfonate of 3-[(dimethylamino)methyl]-N-{2-[4-(hydroxycarbamoyl)phenoxy]ethyl}-1-benzofuran-2-carboxamide produced using the method according to the invention, which is characterized by a powder X-ray diffraction diagram exhibiting the following diffraction lines (Bragg angle 2 theta, expressed in degrees±0.2°) 6.87; 10.71; 11.31; 13.97; 18.51; 21.49; 21.84; 24.56. More particularly, the crystalline form of the naphthalene-1,5-disulfonate of 3-[(dimethylamino)methyl]-N-{2-[4-(hydroxycarbamoyl)phenoxy]ethyl}-1-benzofuran-2-carboxamide is characterized by the following diffraction lines: 6.87; 10.71; 11.31; 13.97; 18.51; 20.71; 21.18; 21.49; 21.84; 22.74; 24.56.

More specifically, the crystalline form of the naphthalene-1,5-disulfonate of 3-[(dimethylamino)methyl]-N-{2-[4-(hydroxycarbamoyl)phenoxy]ethyl}-1-benzofuran-2-carboxamide is characterized by the powder X-ray diffraction diagram below, measured using a PANalytical X'Pert Pro MPD diffractometer with an X'Celerator detector, and expressed in terms of line position (Bragg angle 2 theta, expressed in degrees±0.2°) and interplanar spacing d (expressed in Å):

| Line no. | Angle 2 theta (degrees) | Interplanar spacing (Å) |
|---|---|---|
| 1 | 6.87 | 12.861 |
| 2 | 10.71 | 8.262 |
| 3 | 11.31 | 7.821 |
| 4 | 13.97 | 6.341 |
| 5 | 18.51 | 4.794 |
| 6 | 20.71 | 4.288 |
| 7 | 21.18 | 4.194 |
| 8 | 21.49 | 4.134 |
| 9 | 21.84 | 4.069 |
| 10 | 22.74 | 3.910 |
| 11 | 24.56 | 3.625 |

Finally, the crystalline form of the naphthalene-1,5-disulfonate of 3-[(dimethylamino)methyl]-N-{2-[4-(hydroxycarbamoyl)phenoxy]ethyl}-1-benzofuran-2-carboxamide has also been characterized by solid state NMR spectroscopy and the $^{13}C$ CP/MAS (cross polarization/magic angle spinning) spectrum exhibits the following peaks (expressed in ppm±0.2 ppm):

| Peak no. | Chemical shift (ppm) | Δδ ppm (/37.8 ppm) |
|---|---|---|
| 1 | 167.9 | 130.1 |
| 2 | 161.1 | 123.3 |
| 3 | 158.6 | 120.8 |
| 4 | 153.8 | 116.0 |
| 5 | 145.5 | 107.7 |
| 6 | 142.4 | 104.6 |
| 7 | 130.3 | 92.5 |
| 8 | 126.0 | 88.2 |
| 9 | 122.4 | 84.6 |
| 10 | 119.6 | 81.8 |
| 11 | 114.3 | 76.5 |
| 12 | 64.5 | 26.7 |
| 13 | 51.2 | 13.4 |
| 14 | 45.6 | 7.8 |
| 15 | 44.0 | 6.2 |
| 16 | 37.8 | 0.0 |

In one aspect, provided is a crystalline form of the naphthalene-2-sulfonate of 3-[(dimethylamino)methyl]-N-{2-[(4-(hydroxycarbamoyl)phenoxy]ethyl}-1-benzofuran-2-carboxamide produced using the method according to the invention, which is characterized by a powder X-ray diffraction diagram exhibiting the following diffraction lines (Bragg angle 2 theta, expressed in degrees±0.2°): 8.92; 9.33; 10.85; 17.89; 19.79; 21.79; 26.39.

More particularly, the crystalline form of the naphthalene-2-sulfonate of 3-[(dimethylamino)methyl]-N-{2-[4-(hydroxycarbamoyl)phenoxy]ethyl}-1-benzofuran-2-carboxamide is characterized by the following diffraction lines: 8.92; 9.33; 10.85; 11.78; 17.89; 19.79; 19.99; 21.79; 25.23; 26.39.

More specifically, the crystalline form of the naphthalene-2-sulfonate of 3-[(dimethylamino)methyl]-N-{2-[4-(hydroxycarbamoyl)phenoxy]ethyl}-1-benzofuran-2-carboxamide is characterized by the powder X-ray diffraction diagram below, measured using a PANalytical X'Pert Pro MPD diffractometer with an X'Celerator detector, and expressed in terms of line position (Bragg angle 2 theta, expressed in degrees±0.2°) and interplanar spacing d (expressed in Å):

| Line no. | Angle 2 theta (degrees) | Interplanar spacing (Å) |
|---|---|---|
| 1 | 8.92 | 9.917 |
| 2 | 9.33 | 9.476 |
| 3 | 10.85 | 8.153 |
| 4 | 11.78 | 7.515 |
| 5 | 17.89 | 4.957 |
| 6 | 19.79 | 4.484 |
| 7 | 19.99 | 4.440 |
| 8 | 21.79 | 4.078 |
| 9 | 25.23 | 3.529 |
| 10 | 26.39 | 3.376 |

Finally, the crystalline form of the naphthalene-2-sulfonate of 3-[(dimethylamino)methyl]-N-{2-[4-(hydroxycarbamoyl)phenoxy]ethyl}-1-benzofuran-2-carboxamide has also been characterized by solid state NMR spectroscopy and the $^{13}$C CP/MAS spectrum exhibits the following peaks (expressed in ppm±0.2 ppm):

| Peak no. | Chemical shift (ppm) | Δδ ppm (/41.7 ppm) |
|---|---|---|
| 1 | 165.7 | 124.0 |
| 2 | 154.2 | 112.5 |
| 3 | 141.1 | 99.4 |
| 4 | 139.5 | 97.8 |
| 5 | 133.2 | 91.5 |
| 6 | 128.5 | 86.8 |
| 7 | 127.6 | 85.9 |
| 8 | 126.0 | 84.3 |
| 9 | 124.6 | 82.9 |
| 10 | 122.4 | 80.7 |
| 11 | 113.1 | 71.4 |
| 12 | 64.8 | 23.1 |
| 13 | 63.2 | 21.5 |
| 14 | 50.7 | 9.0 |
| 15 | 47.2 | 5.5 |
| 16 | 45.5 | 3.8 |
| 17 | 42.8 | 1.1 |
| 18 | 41.7 | 0.0 |

In one aspect, provided is a crystalline form of the oxalate of 3-[(dimethylamino)methyl]-N-{2-[4-(hydroxycarbamoyl)phenoxy]ethyl}-1-benzofuran-2-carboxamide produced using the method according to the invention, which is characterized by a powder X-ray diffraction diagram exhibiting the following diffraction lines (Bragg angle 2 theta, expressed in degrees±0.2°): 9.11; 9.67; 16.39; 17.73; 18.49; 18.65; 18.79; 21.96; 22.39; 23.39; 26.76; 27.92; 30.72. More particularly, the crystalline form of the oxalate of 3-[(dimethylamino)methyl]-N-{2-[4-(hydroxycarbamoyl)phenoxy]ethyl}-1-benzofuran-2-carboxamide is characterized by the following diffraction lines: 9.11; 9.67; 16.39; 16.56; 17.73; 18.49; 18.65; 18.79; 20.35; 20.85; 21.00; 21.96; 22.39; 23.39; 23.91; 26.22; 26.76; 27.92; 30.72.

More specifically, the crystalline form of the oxalate of 3-[(dimethylamino)methyl]-N-{2-[4-(hydroxycarbamoyl)phenoxy]ethyl}-1-benzofuran-2-carboxamide is characterized by the powder X-ray diffraction diagram below, measured using a PANalytical X'Pert Pro MPD diffractometer with an X'Celerator detector, and expressed in terms of line position (Bragg angle 2 theta, expressed in degrees±0.2°) and of interplanar spacing d (expressed in Å):

| Line no. | Angle 2 theta (degrees) | Interplanar spacing (Å) |
|---|---|---|
| 1 | 9.11 | 9.704 |
| 2 | 9.67 | 9.142 |
| 3 | 16.39 | 5.408 |
| 4 | 16.56 | 5.354 |
| 5 | 17.73 | 5.004 |
| 6 | 18.49 | 4.798 |
| 7 | 18.65 | 4.758 |
| 8 | 18.79 | 4.721 |
| 9 | 20.35 | 4.364 |
| 10 | 20.85 | 4.260 |
| 11 | 21.00 | 4.229 |
| 12 | 21.96 | 4.048 |
| 13 | 22.39 | 3.971 |
| 14 | 23.39 | 3.804 |
| 15 | 23.91 | 3.722 |
| 16 | 26.22 | 3.399 |
| 17 | 26.76 | 3.332 |
| 18 | 27.92 | 3.196 |
| 19 | 30.72 | 2.911 |

Finally, the crystalline form of the oxalate of 3-[(dimethylamino)methyl]-N-{2-[4-(hydroxycarbamoyl)phenoxy]ethyl}-1-benzofuran-2-carboxamide has also been characterized by solid state NMR spectroscopy and the $^{13}$C CP/MAS spectrum exhibits the following peaks (expressed in ppm±0.2 ppm):

| Peak no. | Chemical shift (ppm) | Δδ ppm (/42.9 ppm) |
|---|---|---|
| 1 | 168.9 | 126.0 |
| 2 | 162.6 | 119.7 |
| 3 | 153.7 | 110.8 |
| 4 | 146.1 | 103.2 |
| 5 | 130.0 | 87.1 |
| 6 | 128.7 | 85.8 |
| 7 | 127.4 | 84.5 |
| 8 | 125.8 | 82.9 |
| 9 | 124.3 | 81.4 |
| 10 | 123.2 | 80.3 |
| 11 | 119.8 | 76.9 |
| 12 | 118.5 | 75.6 |
| 13 | 114.2 | 71.3 |
| 14 | 113.5 | 70.6 |
| 15 | 111.8 | 68.9 |
| 16 | 65.8 | 22.9 |
| 17 | 50.9 | 8.0 |
| 18 | 47.3 | 4.4 |
| 19 | 42.9 | 0.0 |

In one aspect, provided is a novel crystalline form of the benzenesulfonate of 3-[(dimethylamino)methyl]-N-{2-[4-(hydroxycarbamoyl)phenoxy]ethyl}-1-benzofuran-2-carboxamide produced using the method according to the invention, which is characterized by a powder X-ray diffraction diagram exhibiting the following diffraction lines (Bragg angle 2 theta, expressed in degrees±0.2°): 8.08; 10.03; 10.36; 13.63; 15.00; 16.19; 17.73; 17.90; 18.77; 19.77; 21.98; 22.45. More particularly, the crystalline form of the benzenesulfonate of 3-[(dimethylamino)methyl]-N-{2-[4-(hydroxycarbamoyl)phenoxy]ethyl}-1-benzofuran-2-carboxamide is characterized by the following diffraction lines: 8.08; 10.03; 10.36; 11.86; 12.66; 13.63; 15.00; 16.19; 16.39; 16.52; 17.73; 17.90; 18.77; 19.77; 20.20; 20.86; 21.11; 21.98; 22.45; 23.84; 26.13; 26.74; 27.44.

More specifically, the crystalline form of the benzenesulfonate of 3-[(dimethylamino)methyl]-N-{2-[4-(hydroxycarbamoyl)phenoxy]ethyl}-1-benzofuran-2-carboxamide is characterized by the powder X-ray diffraction diagram below, measured using a PANalytical X'Pert Pro MPD diffractometer with an X'Celerator detector, and expressed in terms of line position (Bragg angle 2 theta, expressed in degrees±0.2°) and of interplanar spacing d (expressed in Å):

| Line no. | Angle 2 theta (degrees) | Interplanar spacing (Å) |
|---|---|---|
| 1 | 8.08 | 10.949 |
| 2 | 10.03 | 8.818 |
| 3 | 10.36 | 8.539 |
| 4 | 11.86 | 7.463 |
| 5 | 12.66 | 6.992 |
| 6 | 13.63 | 6.498 |
| 7 | 15.00 | 5.906 |
| 8 | 16.19 | 5.473 |
| 9 | 16.39 | 5.407 |
| 10 | 16.52 | 5.366 |
| 11 | 17.73 | 5.002 |
| 12 | 17.90 | 4.954 |
| 13 | 18.77 | 4.728 |
| 14 | 19.77 | 4.492 |
| 15 | 20.20 | 4.395 |
| 16 | 20.86 | 4.259 |
| 17 | 21.11 | 4.209 |
| 18 | 21.98 | 4.043 |
| 19 | 22.45 | 3.961 |

-continued

| Line no. | Angle 2 theta (degrees) | Interplanar spacing (Å) |
|---|---|---|
| 20 | 23.84 | 3.732 |
| 21 | 26.13 | 3.411 |
| 22 | 26.74 | 3.333 |
| 23 | 27.44 | 3.251 |

Finally, the crystalline form of the benzenesulfonate of 3-[(dimethylamino)methyl]-N-{2-[4-(hydroxycarbamoyl)phenoxy]ethyl}-1-benzofuran-2-carboxamide has also been characterized by solid state NMR spectroscopy and the $^{13}$C CP/MAS spectrum exhibits the following peaks (expressed in ppm±0.2 ppm):

| Peak no. | Chemical shift (ppm) | Δδ ppm (/42.0 ppm) |
|---|---|---|
| 1 | 165.5 | 123.5 |
| 2 | 161.7 | 119.7 |
| 3 | 152.6 | 110.6 |
| 4 | 145.9 | 103.9 |
| 5 | 128.2 | 86.2 |
| 6 | 126.5 | 84.5 |
| 7 | 121.6 | 79.6 |
| 8 | 114.3 | 72.3 |
| 9 | 111.2 | 69.2 |
| 10 | 68.4 | 26.4 |
| 11 | 51.2 | 9.2 |
| 12 | 44.5 | 2.5 |
| 13 | 42.0 | 0.0 |

In another aspect, provided is a crystalline form of the hydrogen sulfate of 3-[(dimethylamino)methyl]-N-{2-[4-(hydroxycarbamoyl)phenoxy]ethyl}-1-benzofuran-2-carboxamide or a hydrate thereof. In one embodiment, the hydrate is a hemipentahydrate. In another embodiment, the hydrate is a hemiheptahydrate.

In one embodiment, the hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide produced using the method according to the invention is characterized by a powder X-ray diffraction diagram exhibiting the hallowing diffraction lines (Bragg angle 2 theta, expressed in degrees±0.2°): 6.92; 9.01; 11.04; 13.87; 14.24; 14.89; 15.06; 17.34; 18.96; 20.05; 21.49; 24.34; 24.59; 25.19; 25.89. More particularly, the hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide is characterized by the following diffraction lines: 6.92; 9.01; 11.04; 11.82; 13.87; 14.24; 14.89; 15.06; 17.34; 18.96; 20.05; 20.34; 21.23; 21.49; 22.68; 22.85; 24.34; 24.59; 25.19; 25.89; 28.28.

More specifically, the hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide is characterized by the powder X-ray diffraction diagram below, measured using a PANalytical X'Pert Pro MPD diffractometer with an X'Celerator detector, and expressed in terms of line position (Bragg angle 2 theta, expressed in degrees±0.2°) and interplanar spacing d (expressed in Å):

| Line no. | Angle 2 theta (degrees) | Interplanar spacing (Å) |
|---|---|---|
| 1 | 6.92 | 12.782 |
| 2 | 9.01 | 9.815 |

-continued

| Line no. | Angle 2 theta (degrees) | Interplanar spacing (Å) |
|---|---|---|
| 3 | 11.04 | 8.015 |
| 4 | 11.82 | 7.489 |
| 5 | 13.87 | 6.386 |
| 6 | 14.24 | 6.222 |
| 7 | 14.89 | 5.949 |
| 8 | 15.06 | 5.882 |
| 9 | 17.34 | 5.114 |
| 10 | 18.96 | 4.681 |
| 11 | 20.05 | 4.429 |
| 12 | 20.84 | 4.262 |
| 13 | 21.23 | 4.185 |
| 14 | 21.49 | 4.134 |
| 15 | 22.68 | 3.920 |
| 16 | 22.85 | 3.892 |
| 17 | 24.34 | 3.657 |
| 18 | 24.59 | 3.620 |
| 19 | 25.19 | 3.535 |
| 20 | 25.89 | 3.441 |
| 21 | 28.28 | 3.156 |

Finally, the hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide has also been characterized by solid state NMR spectroscopy and the $^{13}$C CP/MAS (cross polarization/magic angle spinning) spectrum exhibits the following peaks (expressed in ppm±0.2 ppm):

| Peak no. | Chemical shift (ppm) | Δδ ppm (/38.4 ppm) |
|---|---|---|
| 1 | 166.0 | 127.6 |
| 2 | 159.2 | 120.8 |
| 3 | 146.8 | 108.4 |
| 4 | 123.1 | 84.7 |
| 5 | 121.8 | 83.4 |
| 6 | 120.7 | 82.3 |
| 7 | 114.8 | 76.4 |
| 8 | 112.8 | 74.4 |
| 9 | 112.1 | 73.7 |
| 10 | 110.0 | 71.6 |
| 11 | 107.1 | 68.7 |
| 12 | 66.7 | 28.3 |
| 13 | 63.0 | 24.6 |
| 14 | 49.0 | 10.6 |
| 15 | 41.7 | 3.3 |
| 16 | 40.2 | 1.8 |
| 17 | 38.4 | 0.0 |

In one embodiment, the hemiheptahydrate crystalline form of the hydrogen sulfate of 3-[(dimethylamino)methyl]-N-{2-[4-(hydroxycarbamoyl)phenoxy]ethyl}-1-benzofuran-2-carboxamide produced using the method according to the invention is characterized by a powder X-ray diffraction diagram exhibiting the following diffraction lines (Bragg angle 2 theta, expressed in degrees±0.2°): 9.99; 10.67; 13.79; 13.92; 14.25; 14.67; 15.18; 16.21; 18.44; 18.82; 20.42; 21.71; 22.47; 23.30; 24.25. More particularly, the hemiheptahydrate crystalline form of the hydrogen sulfate of 3-[(dimethylamino)methyl]-N-{2-[4-(hydroxycarbamoyl)phenoxy]ethyl}-1-benzofuran-2-carboxamide is characterized by the following diffraction lines: 9.99; 10.67; 12.65; 13.79; 13.92; 14.25; 14.67; 15.18; 16.21; 16.43; 18.44; 18.82; 20.42; 20.76; 21.09; 21.45; 21.71; 22.47; 22.92; 23.30; 23.89; 24.25; 26.02; 26.54.

More specifically, the hemiheptahydrate crystalline form of the hydrogen sulfate of 3-[(dimethylamino)methyl]-N-{2-[4-(hydroxycarbamoyl)phenoxy]ethyl}-1-benzofuran-2-carboxamide is characterized by the powder X-ray diffraction diagram below, measured using a PANalytical X'Pert Pro MPD diffractometer with an X'Celerator detector, and expressed in terms of line position (Bragg angle 2 theta, expressed in degrees±0.2°) and interplanar spacing d (expressed in Å):

| Line no. | Angle 2 theta (degrees) | Interplanar spacing (Å) |
|---|---|---|
| 1 | 9.99 | 8.838 |
| 2 | 10.67 | 8.284 |
| 3 | 12.65 | 6.995 |
| 4 | 13.79 | 6.418 |
| 5 | 13.92 | 6.356 |
| 6 | 14.25 | 6.211 |
| 7 | 14.67 | 6.032 |
| 8 | 15.18 | 5.831 |
| 9 | 16.21 | 5.464 |
| 10 | 16.43 | 5.389 |
| 11 | 18.44 | 4.808 |
| 12 | 18.82 | 4.712 |
| 13 | 20.42 | 4.345 |
| 14 | 20.76 | 4.276 |
| 15 | 21.09 | 4.209 |
| 16 | 21.45 | 4.140 |
| 17 | 21.71 | 4.090 |
| 18 | 22.47 | 3.953 |
| 19 | 22.92 | 3.877 |
| 20 | 23.30 | 3.814 |
| 21 | 23.89 | 3.721 |
| 22 | 24.25 | 3.667 |
| 23 | 26.02 | 3.422 |
| 24 | 26.54 | 3.355 |

The invention also extends to the method for preparing salts of 3-[(dimethylamino)methyl]-N-{2-[4-(hydroxycarbamoyl)phenoxy]ethyl}-1-benzofuran-2-carboxamide in a well-defined crystalline form, characterized in that the 3-[(dimethylamino)methyl]-N-{2-[4-(hydroxycarbamoyl)phenoxy]ethyl}-1-benzofuran-2-carboxamide is crystallised in a polar medium in the presence of naphthalene-1,5-disulfonic acid, naphthalene-2-sulfonic acid, oxalic acid or benzenesulfonic acid. The polar medium preferably consists of one or more solvents chosen from among water, alcohols, ketones, nitriles and esters. As used herein:
- "alcohols" are understood to mean $C_1$-$C_6$ alcohols such as methanol, ethanol, propanol, isopropanol, butanol, isobutanol, pentanol, 2-pentanol, 3-pentanol, isopentanol, hexanol;
- "ketones" are understood to mean $C_3$-$C_6$ ketones such as acetone, methylethyl ketone, 2-pentanone, 3-pentanone, 3-methyl-2-butanone, 2-hexanone, 3-hexanone, ethylisopropylketone, methylisopropylketone, 2,2-dimethyl-3-butanone;
- "nitriles" are understood to mean acetonitrile, acrylonitrile, propanenitrile or benzonitrile;
- "esters" are understood to mean $C_3$-$C_8$ esters such as ethyl formate, isopropyl formate, ethyl acetate, propyl acetate, isopropyl acetate, butyl acetate, isobutyl acetate, tert-butyl acetate, pentyl acetate, isopentyl acetate, hexyl acetate.

The preferred alcohols are ethanol and isopropanol. Among the solvents, acetone and methylethylketone are the preferred ketones, ethyl acetate is the preferred ester and acetonitrile is the preferred nitrile.

Alternatively, the polar medium is a binary mixture, one of the components of which is water. Even more preferably, the polar medium is a binary mixture selected from among: acetone/water, ethanol/water, isopropanol/water and methylethylketone/water.

In the crystallization method according to the invention, it is possible to use 3-[(dimethylamino)methyl]-N-{2-[4-(hydroxycarbamoyl)phenoxy]ethyl}-1-benzofuran-2-carboxamide (free base) obtained by any method.

The invention also extends to another method for preparation of the crystalline forms of the salts of 3-[(dimethylamino)methyl]-N-{2-[4-(hydroxycarbamoyl)phenoxy]ethyl}-1-benzofuran-2-carboxamide according to the invention, in which the crystallization of the 3-[(dimethylamino)methyl]-N-{2-[4-(hydroxycarbamoyl)phenoxy]ethyl}-1-benzofuran-2-carboxamide (free base) is initiated by seeding of a very small quantity of crystalline forms of the salts of 3-[(dimethylamino)methyl]-N-{2-[4-(hydroxycarbamoyl)phenoxy]ethyl}-1-benzofuran-2-carboxamide according to the invention, this reaction being carried out in a polar medium and in the presence of the corresponding acid. In this second crystallization method according to the invention, it is also possible to use 3-[(dimethylamino)methyl]-N-{2-[4-(hydroxycarbamoyl)phenoxy]ethyl}-1benzofuran-2-carboxamide (free base) obtained by any method.

Obtaining crystalline forms of the novel salts of 3-[(dimethylamino)methyl]-N-{2-[4-(hydroxycarbamoyl)phenoxy]ethyl}-1-benzofuran-2-carboxamide according to the invention has the advantage of enabling, the preparation of pharmaceutical formulations which have a constant and reproducible composition and exhibit good characteristics of dissolution and of stability, which is particularly advantageous when the formulations are intended for oral administration. More precisely, the use of crystalline forms of the novel salts of 3-[(dimethylamino)methyl]-N-{2-[4-(hydroxycarbamoyl)phenoxy]ethyl}-1-benzofuran-2-carboxamide according to the invention is particularly advantageous on an industrial scale taking account of their low hygroscopicity.

The invention also extends to the process for preparation of the hydrogen sulfate of 3-[(dimethylamino)methyl]-N-{2-[4-(hydroxycarbamoyl)phenoxy]ethyl}-1-benzofuran-2-carboxamide in two well defined hydrated crystalline forms, characterized in that the 3-[(dimethylamino)methyl]-N-{2-[4-(hydroxycarbamoyl)phenoxy]ethyl}-1-benzofuran-2-carboxamide is crystallised in a polar medium in the presence of sulfuric acid. The polar medium preferably consists of one or more solvents chosen from among water, ketones, nitriles and esters.

Among the preferred solvents, use will be made of acetone and methylethylketone for ketones and ethyl acetate foresters. Water is a particularly preferred solvent.

Alternatively, the polar medium is a binary mixture of which one of the components is water. Even more preferably, the polar medium is a hydro-alcoholic mixture. Advantageously, the polar medium is a binary mixture selected from among: acetone/water, ethanol/water, isopropanol/water and methylethylketone/water.

In the crystallization process according to the invention, it is possible to use 3-[(dimethylamino)methyl]-N-{2-[4-(hydroxycarbamoyl)phenoxy]ethyl}-1-benzofuran-2-carboxamide (free base) obtained by any method.

The invention likewise extends to another process for preparation of the hydrogen sulfate of 3-[(dimethylamino)methyl]-N-{2-[4-(hydroxycarbamoyl)phenoxy]ethyl}-1-benzofuran-2-carboxamide in two well defined hydrated crystalline forms, wherein the crystallization of the 3-[(dimethylamino)methyl]-N-{2-[4-(hydroxycarbamoyl)phenoxy]ethyl}-1-benzofuran-2-carboxamide (free base) is initiated by seeding of a very small quantity of the hydrated crystalline form of the hydrogen sulfate of 3-[(dimethylamino)methyl]-N-{2-[4-(hydroxycarbamoyl)phenoxy]ethyl}-1-benzofuran-2-carboxamide according to the invention, this reaction being carried out in a polar medium and in the presence of sulfuric acid. In this second crystallization process according to the invention, it is also possible to use 3-[(dimethylamino)methyl]-N-{2-[4-(hydroxycarbamoyl) phenoxy]ethyl}-1-benzofuran-2-carboxamide (free base) obtained by any method.

Obtaining hydrated crystalline forms of the hydrogen sulfate of 3-[(dimethylamino)methyl]-N-{2-[4-(hydroxycarbamoyl)phenoxy]ethyl}-1-benzofuran-2-carboxamide according to the invention has the advantage of being easily manipulated and enabling the preparation of pharmaceutical formulations which have a constant and reproducible composition whilst exhibiting good characteristics of dissolution and of stability, which is particularly advantageous when the formulations are intended for oral administration. More precisely, the use of hydrated crystalline forms of the hydrogen sulfate of 3-[(dimethylamino)methyl]-N-{2-[4-(hydroxycarbamoyl)phenoxy]ethyl}-1-benzofuran-2-carboxamide according to the invention is particularly advantageous on an industrial scale.

The crystalline forms (including the hydrated crystalline forms) of the novel salts of 3-[(dimethylamino)methyl]-N-{2-[4-(hydroxycarbamoyl)phenoxy]ethyl}-1-benzofuran-2-carboxamide according to the invention are intended for the treatment of cancer and, more particularly, for the treatment of a carcinoma, a tumor, a neoplasm, a lymphoma, a melanoma, a glioma, a sarcoma or a blastoma.

The invention also extends to pharmaceutical compositions including as active principle a salt of 3-[(dimethylamino)methyl]-N-{2-[4-(hydroxycarbamoyl)phenoxy] ethyl}-1-benzofuran-2-carboxamide according to the formula (I) and, even more particularly, the crystalline forms (including the hydrated crystalline forms) of salts of 3-[(dimethylamino)methyl]-N-{2-[4-(hydroxycarbamoyl)phenoxy]ethyl}-1-benzofuran-2-carboxamide according to the invention, with one or more appropriate non-toxic inert carriers. Among the pharmaceutical compositions according to the invention, mention may be made more particularly of those which are suitable for oral, parenteral (intravenous or subcutaneous) or nasal administration, plain or coated tablets, granules, sublingual tablets, capsules, pills, suppositories, creams, ointments, dermal gels, injectable preparations, drinkable suspensions and chewing gums.

Orally administered pharmaceutical compositions are preferred.

The useful dosage varies according to the sex, age and weight of the patient, the administration route, the nature of the cancer and any associated treatments, and the useful dosage ranges between 20 mg and 480 mg of 3-[(dimethylamino)methyl]-N-{2-[4-(hydroxycarbamoyl)phenoxy] ethyl}-1-benzofuran-2-carboxamide expressed in free base per day.

The examples below illustrate the invention but do not limit it in any way.

EXAMPLE 1

Method for Producing the Crystalline Form of the naphthalene-1,5-disulfonate of 3-[(dimethylamino) methyl]-N-{2-[4-(hydroxycarbamoyl)phenoxy] ethyl}-1-benzofuran-2-carboxamide In a 50 mL flask, an equivalent of 3-[(dimethylamino) methyl]-N-{2-[4-(hydroxycarbamoyl)phenoxy]ethyl}-1-benzofuran-2-carboxamide (free base) (1245.0 mg; 3.133 mmol) was added, followed by a half-equivalent of naphthalene-1,5-disulfonic acid tetrahydrate (564.5 mg; 1.566 mmol). Then 25 mL of isopropanol were added and the reaction mixture was subjected to sustained magnetic stirring at 60° C. for 1 hour. Next the reaction mixture was cooled under sustained magnetic stirring to 10° C. at a speed between 1 and 1.5° C./min, then maintained for approximately 1 day at 10° C. After filtration on a porosity 3 glass frit, the solid was dried in a desiccator in vacuo (100 mbar) in order to give the compound of the title with an output of 96%. The solid was characterized by the powder X-ray diffraction diagram and the NMR spectrum detailed in the following Examples 7 and 9.

EXAMPLE 2

Method for Producing the Crystalline form Of the naphthalene-2-sulfonate of 3-[(dimethylamino) methyl]-N-{2-[4-(hydroxycarbamoyl)phenoxy] ethyl}-1-benzofuran-2-carboxamide In a 50 mL flask, an equivalent of 3-[(dimethylamino) methyl]-N-{2-[4-(hydroxycarbamoyl)phenoxy]ethyl}-1-benzofuran-2-carboxamide (free base) (1115.5 mg; 2.807 mmol) was added, followed by an equivalent of naphthalene-2-sulfonic acid monohydrate (635.9 mg; 2.806 mmol). Then 25 mL of acetonitrile were added and the reaction mixture was subjected to sustained magnetic stirring at 60° C. for 1 hour. Next the reaction mixture was cooled under sustained magnetic stirring to 10° C. at a speed between 1 and 1.5° C./min, then maintained for approximately 1 day at 10° C. After filtration on a porosity 3 glass frit, the solid was dried in a desiccator in vacuo (100 mbar) in order to give the compound of the title with an output of 96%. The solid was characterized by the powder X-ray diffraction diagram and the NMR spectrum detailed in the following Examples 7 and 9.

EXAMPLE 3

Method for Producing the Crystalline Form of the Oxalate of 3-[(dimethylamino)methyl]-N-{2-[4-hydroxycarbamoyl)phenoxy]ethyl}-1-benzofuran-2-carboxamide In a 50 mL flask, an equivalent of 3-[(dimethylamino) methyl]-N-{2-[4-(hydroxycarbamoyl)phenoxy]ethyl}-1-carboxamide (free base) (1382.8 mg; 3.479 mmol) was added, followed by an equivalent of oxalic acid, (313.1 mg; 3.477 mmol). Then 25 mL of ethanol were added and the reaction mixture was subjected to sustained magnetic stirring at 60° C. for 1 hour. Next the reaction mixture was cooled under sustained magnetic stirring to 10° C. at a speed between 1 and 1.5° C./min, then maintained for approximately 1 day at 10° C. After filtration on a porosity 3 glass frit, the solid was dried in a desiccator in vacuo (100 mbar) in order to give the compound of the title with an output of 95%. The solid was characterized by the powder X-ray diffraction diagram and the NMR spectrum detailed in the following Examples 7 and 9.

EXAMPLE 4

Method for Producing the Crystalline form of the Benzenesulfonate of 3-[(dimethylamino)methyl]-N-{2-[4-(hydroxycarbamoyl)phenoxy]ethyl}-1-benzofuran-2-carboxamide In a 100 mL flask, an equivalent of 3-[(dimethylamino) methyl]-N-{2-[4-(hydroxycarbamoyl)phenoxy]ethyl}-1- benzofuran-2-carboxamide (free base) (1496 mg; 3.746 mmol) was added, followed by 35 mL of isopropanol and 5 mL of water. The mixture was brought to reflux. Then an equivalent of benzenesulfonic acid (599 mg; 3.787 mmol) were added and the reaction mixture was held at reflux under sustained magnetic stirring for 1 hour. Next the reaction mixture was cooled under sustained magnetic stirring to ambient temperature then maintained for approximately 1 hour at ambient temperature. After filtration on a disposable Chemrus 10 μm frit and rinsing with 2×1 mL of isopropanol, the solid was dried in an oven at 40° C. in vacuo (10 mbar) for 24 hours in order to give the compound of the title with a yield of 83%. The solid was characterized by the powder X-ray diffraction diagram and the NMR spectrum detailed in the following Examples 7 and 9.

EXAMPLE 5

Method for Producing the Hemipentahydrate Crystalline Form of the Hydrogen Sulfate of 3-[(dimethylamino)methyl]-N-{2-[4-(hydroxycarbamoyl)phenoxy]ethyl}-1-benzofuran-2-carboxamide In a 50 mL flask, an equivalent of 3-[(dimethylamino)methyl]-N-{2-[4-(hydroxycarbamoyl)phenoxy]ethyl}-1-benzofuran-2-carboxamide (free base) (1512.8 mg; 3.807 mmol) was added, followed by a half-equivalent of sulfuric acid (5.302 mL of an aqueous solution at 0.359 mol·L$^{-1}$; 1.903 mmol). The mixture was subjected to a magnetic stirring until a clear solution is obtained. The water was then evaporated under a stream of air. The white powder was then resuspended with 25 mL of n-heptane and the reaction mixture was subjected to sustained magnetic stirring at 60° C. for 1 hour. Next the reaction mixture was cooled under sustained magnetic stirring to 10° C. at a speed between 1 and 1.5° C./min, then maintained for approximately 1 day at 10° C. After filtration on a porosity 3 glass frit, the solid was dried in a desiccator in vacuo (100 mbar) in order to give the compound of the title with an output of 96%. The solid was characterized by the powder X-ray diffraction diagram and the NMR spectrum detailed in the following Examples 7 and 9.

EXAMPLE 6

Method for Producing the Hemiheptahydrate Crystalline Form of the Hydrogen Sulfate of 3-[(dimethylamino)methyl]-N-{2-[4-(hydroxycarbamoyl)phenoxy]ethyl}-1-benzofuran-2-carboxamide A vial containing 100 mg of hydrogen sulfate of 3-[(dimethylamino)methyl]-N-{2-[4-(hydroxycarbamoyl)phenoxy]ethyl}-1-benzofuran-2-carboxamide, hemipentahydrate placed for 3 days in a bell jar containing a saturated saline solution of $KNO_3$ (90% relative humidity) at ambient temperature led to the formation of the compound of the title with a quantitative yield. The resulting solid was characterized by the powder X-ray diffraction diagram detailed in the following Example 7.

EXAMPLE 7

Powder X-ray Diffraction Diagrams of the Crystalline Forms of the Salts of 3-[(dimethylamino)methyl]-N-{2-[4-(hydroxycarbamoyl)phenoxy]ethyl}-1-benzofuran-2-carboxamide According to the Invention The recording of the data was performed on a PANalytical X'Pert Pro MPD diffractometer with an X'Celerator detector under the following conditions:
Voltage 45 kV, current 40 mA;
Mounting theta/theta;
Anode: copper;
K alpha-1 wavelength: 1.54060 Å;
K alpha-2 wavelength: 1.54443 Å;
K alpha-2/K alpha-1 ratio: 0.5;
Measurement mode: continuous from 3° to 55° (Bragg angle 2 theta) with incrementation by 0.017°;
Acquisition time: 15 min.

Crystalline Form of the naphthalene-1,5-disulfonate of 3[(dimethylamino)methyl]-N-{2-[4-(hydroxycarbamoyl)phenoxy]ethyl}-1-benzofuran-2-carboxamide The powder X-ray diffraction diagram of the crystalline form of the naphthalene-1,5-disulfonate of 3-[(dimethylamino)methyl]-N-{2-[4-hydroxycarbamoyl)phenoxy]ethyl}-1-benzofuran-2-carboxamide produced using the method according to Example 1 is expressed in terms of line position (Bragg angle 2 theta, expressed in degrees±0.2°) and of interplanar spacing d (expressed in Å). The significant lines are set out in the following table:

| Line no. | Angle 2 theta (degrees) | Interplanar spacing (Å) |
| --- | --- | --- |
| 1 | 6.87 | 12.861 |
| 2 | 10.71 | 8.262 |
| 3 | 11.31 | 7.821 |
| 4 | 13.97 | 6.341 |
| 5 | 18.51 | 4.794 |
| 6 | 20.71 | 4.288 |
| 7 | 21.18 | 4.194 |
| 8 | 21.49 | 4.134 |
| 9 | 21.84 | 4.069 |
| 10 | 22.74 | 3.910 |
| 11 | 24.56 | 3.625 |

Crystalline Form of the naphthalene-2-sulfonate of 3-[(dimethylamino)methyl]-N-{2-[4-hydroxycarbamoyl)phenoxy]ethyl}-1-benzofuran-2-carboxamide The powder X-ray diffraction diagram of the crystalline form of the naphthalene-2-sulfonate of 3-[(dimethylamino)methyl]-N-{2-[4-(hydroxycarbamoyl)phenoxy]ethyl}-1-benzofuran-2-carboxamide produced using the method according to Example 2 is expressed in terms of line position (Bragg angle 2 theta, expressed in degrees±0.2°) and of interplanar spacing d (expressed in Å). The significant lines are set out in the following table:

| Line no. | Angle 2 theta (degrees) | Interplanar spacing (Å) |
| --- | --- | --- |
| 1 | 8.92 | 9.917 |
| 2 | 9.33 | 9.476 |
| 3 | 10.85 | 8.153 |
| 4 | 11.78 | 7.515 |
| 5 | 17.89 | 4.957 |
| 6 | 19.79 | 4.484 |
| 7 | 19.99 | 4.440 |
| 8 | 21.79 | 4.078 |

| Line no. | Angle 2 theta (degrees) | Interplanar spacing (Å) |
|---|---|---|
| 9 | 25.23 | 3.529 |
| 10 | 26.39 | 3.376 |

Crystalline Form of the Oxalate of 3-[(dimethylamino)methyl]-N-{2-[4-(hydroxycarbamoyl)phenoxy]ethyl}-1-benzofuran-2-carboxamide The powder X-ray diffraction diagram of the crystalline form of the oxalate of 3-[(dimethylamino)methyl]-N-{2-[4-(hydroxycarbamoyl)phenoxy]ethyl}-1-benzofuran-2-carboxamide produced using the method according to Example 3 is expressed in terms of line position (Bragg angle 2 theta, expressed in degrees±0.2°) and of interplanar spacing d (expressed in Å). The significant lines are set out in the following table:

| Line no. | Angle 2 theta (degrees) | Interplanar spacing (Å) |
|---|---|---|
| 1 | 9.11 | 9.704 |
| 2 | 9.67 | 9.142 |
| 3 | 16.39 | 5.408 |
| 4 | 16.56 | 5.354 |
| 5 | 17.73 | 5.004 |
| 6 | 18.49 | 4.798 |
| 7 | 18.65 | 4.758 |
| 8 | 18.79 | 4.721 |
| 9 | 20.35 | 4.364 |
| 10 | 20.85 | 4.260 |
| 11 | 21.00 | 4.229 |
| 12 | 21.96 | 4.048 |
| 13 | 22.39 | 3.971 |
| 14 | 23.39 | 3.804 |
| 15 | 23.91 | 3.722 |
| 16 | 26.22 | 3.399 |
| 17 | 26.76 | 3.332 |
| 18 | 27.92 | 3.196 |
| 19 | 30.72 | 2.911 |

Crystalline Form of the Benzenesulfonate of 3-[(dimethylamino)methyl]-N-{2-[4-(hydroxycarbamoyl)phenoxy]ethyl}-1-benzofuran-2-carboxamide The powder X-ray diffraction diagram of the crystalline form of the benzenesulfonate of 3-[(dimethylamino)methyl]-N-{2-[4-(hydroxycarbamoyl)phenoxy]ethyl}-1-benzofuran-2-carboxamide produced using the method according to Example 4 is expressed in terms of line position (Bragg angle 2 theta, expressed in degrees±0.2°) and of interplanar spacing d (expressed in Å). The significant lines are set out in the following table:

| Line no. | Angle 2 theta (degrees) | Interplanar spacing (Å) |
|---|---|---|
| 1 | 8.08 | 10.949 |
| 2 | 10.03 | 8.818 |
| 3 | 10.36 | 8.539 |
| 4 | 11.86 | 7.463 |
| 5 | 12.66 | 6.992 |
| 6 | 13.63 | 6.498 |
| 7 | 15.00 | 5.906 |
| 8 | 16.19 | 5.473 |
| 9 | 16.39 | 5.407 |
| 10 | 16.52 | 5.366 |
| 11 | 17.73 | 5.002 |
| 12 | 17.90 | 4.954 |
| 13 | 18.77 | 4.728 |
| 14 | 19.77 | 4.492 |
| 15 | 20.20 | 4.395 |
| 16 | 20.86 | 4.259 |
| 17 | 21.11 | 4.209 |
| 18 | 21.98 | 4.043 |
| 19 | 22.45 | 3.961 |
| 20 | 23.84 | 3.732 |
| 21 | 26.13 | 3.411 |
| 22 | 26.74 | 3.333 |
| 23 | 27.44 | 3.251 |

Hemipentahydrate Crystalline Form of the Hydrogen Sulfate of 3-[(dimethylamino)methyl]-N-{2-[4-(hydroxycarbamoyl)phenoxy]ethyl}-1-benzofuran-2-carboxamide:

The powder X-ray diffraction diagram of the hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide produced using the method according to Example 5 is expressed in terms of line position (Bragg angle 2 theta, expressed in degrees±0.2°) and of interplanar spacing d (expressed in Å). The significant lines are set out in the following table:

| Line no. | Angle 2 theta (degrees) | Interplanar spacing (Å) |
|---|---|---|
| 1 | 6.92 | 12.782 |
| 2 | 9.01 | 9.815 |
| 3 | 11.04 | 8.015 |
| 4 | 11.82 | 7.489 |
| 5 | 13.87 | 6.386 |
| 6 | 14.24 | 6.222 |
| 7 | 14.89 | 5.949 |
| 8 | 15.06 | 5.882 |
| 9 | 17.34 | 5.114 |
| 10 | 18.96 | 4.681 |
| 11 | 20.05 | 4.429 |
| 12 | 20.84 | 4.262 |
| 13 | 21.23 | 4.185 |
| 14 | 21.49 | 4.134 |
| 15 | 22.68 | 3.920 |
| 16 | 22.85 | 3.892 |
| 17 | 24.34 | 3.657 |
| 18 | 24.59 | 3.620 |
| 19 | 25.19 | 3.535 |
| 20 | 25.89 | 3.441 |
| 21 | 28.28 | 3.156 |

Hemiheptahydrate Crystalline Form of the Hydrogen Sulfate of 3-[(dimethylamino)methyl]-N-{2-[4-(hydroxycarbamoyl)phenoxy]ethyl}-1-benzofuran-2-carboxamide:

The powder X-ray diffraction diagram of the hemiheptahydrate crystalline form of the hydrogen sulfate of 3-[(dimethylamino)methyl]-N-{2-[4-(hydroxycarbamoyl)phenoxy]ethyl}-1-benzofuran-2-carboxamide produced using the method according to Example 6 is expressed in terms of line position (Bragg angle 2 theta, expressed in degrees±0.2°) and of interplanar spacing d (expressed in Å). The significant lines are set out in the following table:

| Line no. | Angle 2 theta (degrees) | Interplanar spacing (Å) |
|---|---|---|
| 1 | 9.99 | 8.838 |
| 2 | 10.67 | 8.284 |
| 3 | 12.65 | 6.995 |
| 4 | 13.79 | 6.418 |
| 5 | 13.92 | 6.356 |
| 6 | 14.25 | 6.211 |
| 7 | 14.67 | 6.032 |
| 8 | 15.18 | 5.831 |
| 9 | 16.21 | 5.464 |

-continued

| Line no. | Angle 2 theta (degrees) | Interplanar spacing (Å) |
| --- | --- | --- |
| 10 | 16.43 | 5.389 |
| 11 | 18.44 | 4.808 |
| 12 | 18.82 | 4.712 |
| 13 | 20.42 | 4.345 |
| 14 | 20.76 | 4.276 |
| 15 | 21.09 | 4.209 |
| 16 | 21.45 | 4.140 |
| 17 | 21.71 | 4.090 |
| 18 | 22.47 | 3.953 |
| 19 | 22.92 | 3.877 |
| 20 | 23.30 | 3.814 |
| 21 | 23.89 | 3.721 |
| 22 | 24.25 | 3.667 |
| 23 | 26.02 | 3.422 |
| 24 | 26.54 | 3.355 |

EXAMPLE 8

Determination of the Lattices of the Crystalline Forms of the Salts of 3-[(dimethylamino)methyl]-N-{2-[4-(hydroxycarbamoyl)phenoxy]ethyl}-1-benzofuran-2-carboxamide According to the Invention The crystalline structure was determined on the powders obtained in the preceding examples using a PANalytical X'Pert Pro MPD diffractometer with an X'Celerator detector. The following parameters were established:

| Salts | Lattice parameters | Space group |
| --- | --- | --- |
| Naphthalene-1,5-disulfonate (produced using the method according to Example 1) | a = 10.586 Å<br>b = 13.897 Å<br>c = 9.879 Å<br>α = 93.150°<br>β = 102.358°<br>γ = 110.806° | P -1 |
| Oxalate (produced using the method according to Example 3) | a = 5.594 Å<br>b = 20.711 Å<br>c = 20.285 Å<br>β = 107.081 | P 1 2$_1$/c 1 |
| Benzenesulfonate (produced using the method according to Example 4) | a = 10.816 Å<br>b = 13.965 Å<br>c = 19.784 Å<br>β = 117.490° | P 1 2$_1$/c 1 |
| Hydrogen sulfate, hemipentahydrate (produced using the method according to Example 5) | a = 13.123 Å<br>b = 14.696 Å<br>c = 12.967 Å<br>α = 99.965°<br>β = 103.304°<br>γ = 90.348° | P -1 |

EXAMPLE 9

Solid State NMR Spectrum of the Crystalline Forms of the Salts of 3-[(dimethylamino)methyl]-N-{2-[4-(hydroxycarbamoyl)phenoxy]ethyl}-1-benzofuran-2-carboxamide according to the invention The $^{13}$C NMR spectra were recorded at ambient temperature using a Bruker SB Avance III HD 400 spectrometer with a probe of the 4 mm CP/MAS SB VTN type under the following conditions:
Frequency: 100.65 MHz;
Spectral width: 40 kHz;
Magic angle spinning rate of sample: 10 kHz;
Pulse sequence: CP (Cross Polarization) with SPINAL64 decoupling;
Repetition delay: 10 s;
Acquisition time: 46 ms;
Contact time: 4 ms;
Number of scans: 4096.

An apodization function ("10 Hz line broadening") was applied before the Fourier transform. The spectra thus obtained were referenced relative to a sample of adamantane as external sample (the highest-frequency peak of adamantane has a chemical shift of 38.5 ppm). The peaks observed are expressed in ppm±0.2 ppm.

Δδ ppm: Δδ corresponds to the chemical shift difference between the indexed peak and the peak with the lowest referenced chemical shift.

Crystalline Form of the naphthalene-1,5-disulfonate of 3-[(dimethylamino)methyl]-N-{2-[4-(hydroxycarbamoyl)phenoxy]ethyl}-1-benzofuran-2-carboxamide The crystalline form of the naphthalene-1,5-disulfonate of 3-[(dimethylamino)methyl]-N-{2-[4-(hydroxycarbamoyl)phenoxy]ethyl}-1-benzofuran-2-carboxamide produced using the method according to Example 1 exhibits the following peaks:

| Peak no. | Chemical shift (ppm) | Δδ ppm (/37.8 ppm) |
| --- | --- | --- |
| 1 | 167.9 | 130.1 |
| 2 | 161.1 | 123.3 |
| 3 | 158.6 | 120.8 |
| 4 | 153.8 | 116.0 |
| 5 | 145.5 | 107.7 |
| 6 | 142.4 | 104.6 |
| 7 | 130.3 | 92.5 |
| 8 | 126.0 | 88.2 |
| 9 | 122.4 | 84.6 |
| 10 | 119.6 | 81.8 |
| 11 | 114.3 | 76.5 |
| 12 | 64.5 | 26.7 |
| 13 | 51.2 | 13.4 |
| 14 | 45.6 | 7.8 |
| 15 | 44.0 | 6.2 |
| 16 | 37.8 | 0.0 |

Crystalline Form of the naphthalene-2-sulfonate of 3-[(dimethylamino)methyl]-N-{2-[4-(hydroxycarbamoyl)phenoxy]ethyl}-1-benzofuran-2-carboxamide The crystalline form of the naphthalene-2-sulfonate of 3-[(dimethylamino)methyl]-N-{2-[4-(hydroxycarbamoyl)phenoxy]ethyl}-1-benzofuran-2-carboxamide produced using the method according to Example 2 exhibits the following peaks:

| Peak no. | Chemical shift (ppm) | Δδ ppm (/41.7 ppm) |
| --- | --- | --- |
| 1 | 165.7 | 124.0 |
| 2 | 154.2 | 112.5 |
| 3 | 141.1 | 99.4 |
| 4 | 139.5 | 97.8 |
| 5 | 133.2 | 91.5 |
| 6 | 128.5 | 86.8 |
| 7 | 127.6 | 85.9 |
| 8 | 126.0 | 84.3 |
| 9 | 124.6 | 82.9 |
| 10 | 122.4 | 80.7 |
| 11 | 113.1 | 71.4 |
| 12 | 64.8 | 23.1 |
| 13 | 63.2 | 21.5 |
| 14 | 50.7 | 9.0 |
| 15 | 47.2 | 5.5 |
| 16 | 45.5 | 3.8 |
| 17 | 42.8 | 1.1 |
| 18 | 41.7 | 0.0 |

Crystalline Form of the Oxalate of 3-[(dimethylamino) methyl]-N-{2-[4-(hydroxycarbamoyl)phenoxy]ethyl}-1-benzofuran-2-carboxamide The crystalline form of the oxalate of 3-[(dimethylamino) methyl]-N-{2-[4-(hydroxycarbamoyl)phenoy]ethyl}-1-benzofuran-2-carboxamide produced using the method according to Example 3 exhibits the following peaks:

| Peak no. | Chemical shift (ppm) | Δδ ppm (/42.9 ppm) |
|---|---|---|
| 1 | 168.9 | 126.0 |
| 2 | 162.6 | 119.7 |
| 3 | 153.7 | 110.8 |
| 4 | 146.1 | 103.2 |
| 5 | 130.0 | 87.1 |
| 6 | 128.7 | 85.8 |
| 7 | 127.4 | 84.5 |
| 8 | 125.8 | 82.9 |
| 9 | 124.3 | 81.4 |
| 10 | 123.2 | 80.3 |
| 11 | 119.8 | 76.9 |
| 12 | 118.5 | 75.6 |
| 13 | 114.2 | 71.3 |
| 14 | 113.5 | 70.6 |
| 15 | 111.8 | 68.9 |
| 16 | 65.8 | 22.9 |
| 17 | 50.9 | 8.0 |
| 18 | 47.3 | 4.4 |
| 19 | 42.9 | 0.0 |

Crystalline Form of the Benzenesulfonate of 3-[(dimethylamino)methyl]-N-{2-[4-(hydroxycarbamoyl)phenoxy]ethyl}-1-benzofuran-2-carboxamide The crystalline form of the benzenesulfonate of 3-[(dimethylamino)methyl]-N-{2-[4-(hydroxycarbamoyl)phenoxy]ethyl}-1-benzofuran-2-carboxamide produced using the method according to Example 4 exhibits the following peaks:

| Peak no. | Chemical shift (ppm) | Δδ ppm (/42.0 ppm) |
|---|---|---|
| 1 | 165.5 | 123.5 |
| 2 | 161.7 | 119.7 |
| 3 | 152.6 | 110.6 |
| 4 | 145.9 | 103.9 |
| 5 | 128.2 | 86.2 |
| 6 | 126.5 | 84.5 |
| 7 | 121.6 | 79.6 |
| 8 | 114.3 | 72.3 |
| 9 | 111.2 | 69.2 |
| 10 | 68.4 | 26.4 |
| 11 | 51.2 | 9.2 |
| 12 | 44.5 | 2.5 |
| 13 | 42.0 | 0.0 |

The hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide produced using the method according to Example 5 exhibits the following peaks:

| Peak no. | Chemical shift (ppm) | Δδ ppm (/38.4 ppm) |
|---|---|---|
| 1 | 166.0 | 127.6 |
| 2 | 159.2 | 120.8 |
| 3 | 146.8 | 108.4 |
| 4 | 123.1 | 84.7 |
| 5 | 121.8 | 83.4 |
| 6 | 120.7 | 82.3 |
| 7 | 114.8 | 76.4 |
| 8 | 112.8 | 74.4 |
| 9 | 112.1 | 73.7 |
| 10 | 110.0 | 71.6 |
| 11 | 107.1 | 68.7 |
| 12 | 66.7 | 28.3 |
| 13 | 63.0 | 24.6 |
| 14 | 49.0 | 10.6 |
| 15 | 41.7 | 3.3 |
| 16 | 40.2 | 1.8 |
| 17 | 38.4 | 0.0 |

EXAMPLE 10

Hygroscopy

The hygroscopicity of the crystalline forms of the salts of 3-[(dimethylamino)methyl]-N-{2-[4-(hydroxycarbamoyl)phenoxy]ethyl}-1-benzofuran-2-carboxamide according to the invention was evaluated by dynamic vapor sorption (DVS) using a DVS Intrinsic apparatus. A sample of 5 to 10 mg of the substance, weighed accurately, was disposed in a DVS sample pan operating at 25° C. under controlled humidity. The mass variation was recorded on the basis of a balancing bearing at 50% relative humidity, followed by three subsequent linear phases of increasing (from 50 to 90%), of decreasing (from 90 to 0%) and of increasing (from 0 to 50%) the relative humidity at a speed of 10% per hour. The relative humidity was maintained constant when it reached either 0, or 50, or 90% relative humidity, until the mass variation was less than 0.002% per minute, with a time limit of 15 hours.

A mass variation of less than 1% was detected by DVS analysis after exposure of a sample to between 0 and 90% relative humidity at 25° C. for the crystalline form of the naphthalene-1,5-disulfonate of 3-[(dimethylamino)methyl]-N-{2-[4-(hydroxycarbamoyl)phenoxy]ethyl}-1-benzofuran-2-carboxamide produced using the method according to Example 1; the crystalline form of the naphthalene-2-sulfonate of 3-[(dimethylamino)methyl]-N-{2-[4-(hydroxycarbamoyl)phenoxy]ethyl}-1-benzofuran-2-carboxamide produced using the method according to Example 2; and the crystalline form of the benzenesulfonate of 3-[(dimethylamino)methyl]-N-{2-[4-(hydroxycarbamoyl)phenoxy]ethyl}-1-benzofuran-2-carboxamide produced using the method according to Example 4.

A mass variation of less than 0.2% was detected by DVS analysis after exposure of a sample to between 0 and 90% relative humidity at 25° C. for the crystalline form of the oxalate of 3-[(dimethylamino)methyl]-N-{2-[4-(hydroxycarbamoyl)phenoxy]ethyl}-1-benzofuran-2-carboxamide produced using the method according to Example 3.

Consequently, the crystalline forms of the salts of 3-[(dimethylamino)methyl]-N-{2-[4-(hydroxycarbamoyl)phenoxy]ethyl}-1-benzofuran-2-carboxamide produced using the methods of Examples 1 to 4 have a low hygroscopicity enabling a particularly advantageous use thereof on an industrial scale in the preparation of pharmaceutical formulations.

The hygroscopicity of the hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide according to the invention was evaluated by dynamic vapor sorption (DVS) using a DVS Intrinsic apparatus. A sample of 5 to 10 mg of the substance, weighed accurately, was disposed in a DVS sample pan operating at 25° C. under controlled humidity. The mass variation was recorded on the basis of a balancing bearing at 50% relative humidity, followed by three subsequent linear phases of increasing (from 50 to 90%), of decreasing (from 90 to 0%) and of increasing (from 0 to 50%) the relative humidity at a speed of 10% per hour. The relative humidity was maintained constant when it reached either 0, or 50, or 90% relative humidity, until the mass variation is less than 0.002% per minute, with a time limit of 15 hours.

The hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide produced using the method according to Example 5 was stable between 15% relative humidity and 70% relative humidity. Beyond 70% relative humidity, the hemipentahydrate hydrogen sulfate was converted into hemiheptahydrate hydrogen sulfate which was stable between 90% relative humidity and 20% relative humidity. Below 20% relative humidity and to 0% relative humidity, the hemiheptahydrate hydrogen sulfate dehydrated completely and retransformed into hemipentahydrate hydrogen sulfate from 15% relative humidity.

Consequently the hemipentahydrate crystalline form of the hydrogen sulfate of 3-[(dimethylamino)methyl]-N-{2-[4-(hydroxycarbamoyl)phenoxy]ethyl}-1-benzofuran-2-carboxamide produced using the method according to Example 5 has properties which enable it to be easily manipulated—in particular during the preparation of pharmaceutical formulations—over wide ranges of relative humidity values.

EXAMPLE 11

Pharmaceutical Compositions

Formula for preparation of 1000 tablets each containing a dose of 100 mg of 3-[(dimethylamino)methyl]-N-{2-[4-(hydroxycarbamoyl)phenoxy]ethyl}-1-benzofuran-2-carboxamide (expressed as equivalent to the base):

| | |
|---|---|
| Naphthalene-2-sulfonate of 3-[(dimethylamino)methyl]-N-{2-[4-(hydroxycarbamoyl)phenoxy]ethyl}-1-benzofuran-2-carboxamide | 157.1 g |
| Lactose monohydrate | 216.1 g |
| Magnesium stearate | 2.5 g |
| Corn starch | 75 g |
| Maltodextrin | 50 g |
| Anhydrous colloidal silica | 1 g |
| Sodium carboxymethylcellulose | 15 g |

Formula for preparation of 1000 tablets each containing a dose of 100 mg of 3-[(dimethylamino)methyl]-N-{2-[4-(hydroxycarbamoyl)phenoxy]ethyl}-1-benzofuran-2-carboxamide (expressed as equivalent to the base):

| | |
|---|---|
| Benzenesulfonate of 3-[(dimethylamino)methyl]-N-{2-[4-(hydroxycarbamoyl)phenoxy]ethyl}-1-benzofuran-2-carboxamide | 139.8 g |
| Lactose monohydrate | 207.8 g |
| Magnesium stearate | 2.5 g |
| Corn starch | 75 g |
| Maltodextrin | 50 g |
| Anhydrous colloidal silica | 1 g |
| Sodium carboxymethylcellulose | 15 g |

Formula for preparation of 1000 tablets each containing a dose of 100 mg of 3-[(dimethylamino)methyl]-N-{2-[4-(hydroxycarbamoyl)phenoxy]ethyl}-1-benzofuran-2-carboxamide (expressed as equivalent to the base):

| | |
|---|---|
| Oxalate of 3-[(dimethylamino)methyl]-N-{2-[4-(hydroxycarbamoyl)phenoxy]ethyl}-1-benzofuran-2-carboxamide | 122.7 g |
| Lactose monohydrate | 182.3 g |
| Magnesium stearate | 2.5 g |
| Corn starch | 75 g |
| Maltodextrin | 50 g |
| Anhydrous colloidal silica | 1 g |
| Sodium carboxymethylcellulose | 15 g |

Formula for preparation of 1000 tablets each containing a dose of 100 mg of 3-[(dimethylamino)methyl]-N-{2-[4-(hydroxycarbamoyl)phenoxy]ethyl}-1-benzofuran-2-carboxamide (expressed us equivalent to the base):

| | |
|---|---|
| Naphthalene-1,5-disulfonate of 3-[(dimethylamino)methyl]-N-{2-[4-(hydroxycarbamoyl)phenoxy]ethyl}-1-benzofuran-2-carboxamide | 145.4 g |
| Lactose monohydrate | 216.1 g |
| Magnesium stearate | 2.5 g |
| Corn starch | 75 g |
| Maltodextrin | 50 g |
| Anhydrous colloidal silica | 1 g |
| Sodium carboxymethylcellulose | 15 g |

Formula for preparation of 1000 tablets each containing a dose of 100 mg of 3-[(dimethylamino)methyl]-N-{2-[4-(hydroxycarbamoyl)phenoxy]ethyl}-1-benzofuran-2-carboxamide (expressed as equivalent to the base):

| | |
|---|---|
| Hydrogen sulfate of 3-[(dimethylamino)methyl]-N-{2-[4-(hydroxycarbamoyl)phenoxy]ethyl}-1-benzofuran-2-carboxamide | 153.9 g |
| Lactose monohydrate | 228.7 g |
| Magnesium stearate | 2.5 g |
| Corn starch | 75 g |
| Maltodextrin | 50 g |
| Anhydrous colloidal silica | 1 g |
| Sodium carboxymethylcellulose | 15 g |

The invention claimed is:

1. A crystalline form of an abexinostat salt according to formula (Ia)

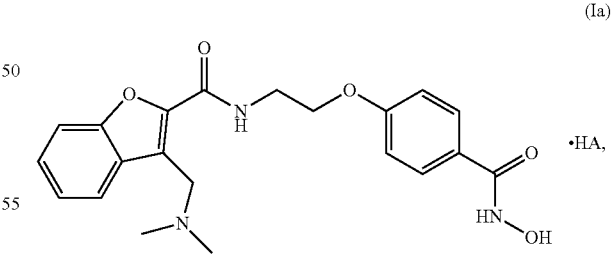

(Ia)

wherein HA is benzenesulfonic acid and wherein the crystalline form has a powder X-ray diffraction diagram exhibiting the following diffraction lines (Bragg angle 2 theta, express in degrees ±0.2°): 8.08; 10.03; 13.63; 15.00; 16.19; 17.73; 17.90; 18.77; 19.77; 21.98; 22.45.

2. The crystalline form of claim 1 characterized in that it has a powder X-ray diffraction diagram exhibiting the following diffraction lines (Bragg angle 2 theta, expressed in degrees ±0.2°): 8.08; 10.03; 11.86; 12.66; 13.63; 15.00;

16.19; 16.39; 16.52; 17.73; 17.90; 18.77; 19.77; 20.20; 20.86; 21.11 21.98; 22.45; 23.84; 26.13; 26.74; 27.44.

3. A pharmaceutical composition comprising the crystalline form of claim 1 as an active ingredient and one or more pharmaceutically acceptable carriers.

4. A pharmaceutical composition comprising the crystalline form of claim 2 as an active ingredient and one or more pharmaceutically acceptable carriers.

* * * * *